United States Patent [19]  
Riesser

[11] 4,143,083  
[45] Mar. 6, 1979

[54] DEHYDROGENATION PROCESS  
[75] Inventor: Gregor H. Riesser, Houston, Tex.  
[73] Assignee: Shell Oil Company, Houston, Tex.  
[21] Appl. No.: 899,040  
[22] Filed: Apr. 24, 1978

Related U.S. Application Data

[63] Continuation-in-part of Ser. No. 787,647, Apr. 14, 1977, abandoned.

[51] Int. Cl.$^2$ .................................................. C07C 5/10  
[52] U.S. Cl. ................................. 260/669 R; 252/470  
[58] Field of Search .................................... 260/669 R

[56] References Cited

U.S. PATENT DOCUMENTS

| | | | |
|---|---|---|---|
| Re. 22,800 | 10/1946 | Kearby | 260/669 R |
| 2,370,798 | 3/1945 | Kearby | 260/669 R |
| 2,395,876 | 3/1946 | Kearby | 260/669 R |
| 2,397,218 | 3/1946 | Sturgeon | 260/669 R |
| 2,414,585 | 1/1947 | Eggertsen et al. | 252/470 |
| 3,084,125 | 4/1963 | Soderquist et al. | 252/470 |
| 3,849,339 | 11/1974 | Turley et al. | 260/669 R |
| 4,039,601 | 8/1977 | Soderquist et al. | 260/669 R |

*Primary Examiner*—C. Davis

[57] ABSTRACT

In the process for effecting a continuous dehydrogenation of hydrocarbons to more unsaturated hydocarbons, particularly alkyl aromatic hydrocarbon to more unsaturated alkyl aromatic hydrocarbons, the improvement which comprises effecting the dehydrogenation with a catalyst comprising a mixture of iron oxide, potassium oxide, carbonate or mixtures thereof, vanadium oxide, optionally chromium oxide and an oxide selected from the group consisting of an oxide of aluminum, cadmium, magnesium, manganese, nickel, a member of the rare earth series, uranium and mixtures thereof.

21 Claims, No Drawings

DEHYDROGENATION PROCESS

This application is a continuation-in-part of copending application Ser. No. 787,647, filed Apr. 14, 1977, and now abandoned.

BACKGROUND OF THE INVENTION

1. Field of the Invention

This invention relates to improved processes for the dehydrogenation of hydrocarbons to corresponding more-unsaturated hydrocarbons, more particularly, to the production of vinyl aromatic hydrocarbons from alkyl aromatic hydrocarbons and to the production of olefins from the corresponding more-saturated aliphatic hydrocarbons utilizing improved catalysts.

2. The Prior Art

The vinyl benzenes and butadienes play a particularly important role in the preparation of synthetic rubbers, plastics and resins. The polymerization of styrene for example with various co-monomers such as butadiene to produce synthetic rubbers is well known as is the polymerization of styrene to produce polystyrene resins.

Styrene and butadiene are typically produced from ethyl benzene and butylene, respectively, by dehydrogenation over solid catalysts in the presence of steam, and at temperatures ranging from 500° to 700° C. The class of catalysts found to be the most effective for this process is a potassium oxide (carbonate) promoted, chromium oxide stabilized, iron oxide material. Considerable research has gone into attempting to improve the activity and selectivity of this class of catalysts. Any improvement which results in either increasing the selectivity (moles of desired product produced per mole of reactant reacted) or the conversion (moles of reactant reacted per mole of starting material) without lowering the other is economically attractive since the result is that the yield (moles of desired product produced per mole of reactant) of the product has been increased. Any increase in the numerical value of the yield results in a more efficient operation with more reactant being converted into the desired product. In commercial operations many of which produce millions of pounds of product per year, a trade-off is frequently effected between selectivity and conversion. An increase of only 1 or 2 percentage points in the selectivity can result in a substantial savings of starting materials. An increase in conversion can substantially reduce capital expenditure and energy consumption. The trade-off may vary depending on raw materials costs, energy costs, and the age of the plant.

The addition of vanadium pentoxide is known to improve the selectivity of the iron-chromium-potassium oxide catalysts. Such catalysts containing vanadium pentoxide were disclosed in U.S. Pat. Nos. 3,361,683 to W. R. Gutmann, issued Jan. 2, 1968 or in 3,084,125 to F. J. Soderquist issued Apr. 2, 1963.

Addition of cobalt to a typical iron-chromium-potassium oxide catalyst has been disclosed in U.S. Pat. No. 3,291,756 to R. S. Bowman, issued Dec. 13, 1966. Copending application Ser. Nos. 740,262 and 740,264 filed Nov. 8, 1976 disclosed the addition of small amounts of cobalt to iron-chromium-potassium-vanadium oxide catalysts. Copending Ser. No. 763,180 filed Jan. 27, 1977, disclosed the addition of small amounts of cobalt to iron-potassium-vanadium oxide catalyst. Belgium Pat. Nos. 811,145 and 811,191, both published June 17, 1974 disclosed the use of cerium in dehydrogenation catalysts. U.S. Pat. No. 3,703,593 to Turley et al. issued Nov. 21, 1972, disclosed the use of manganese as a promoter. U.S. Pat. No. 3,306,942 to Lee, issued Feb. 28, 1967, disclosed the use of magnesium as a promoter. U.S. Pat. No. 3,179,707 to Lee, issued Apr. 20, 1965, disclosed the use of vanadium, manganese, cobalt, cadmium, magnesium, cerium, aluminum and other metals in dehydrogenation catalysts. U.S. Pat. No. 3,505,422 issued Apr. 7, 1970 to Brewer et al. and U.S. Pat. No. 3,424,808 issued Jan. 28, 1969 to Brewer et al. disclosed the use of Group VIII metals, particularly nickel, among others, in dehydrogenation catalysts. U.S. Pat. No. 3,387,053 issued June 4, 1968 to Lee disclosed the use of Group IV to VIII metals in dehydrogenation catalysts. U.S. Pat. No. 3,223,743 issued Dec. 14, 1965 to Alistair disclosed the use of group IV to VIII metals particularly cadmium, manganese, nickel, cesium, aluminum and magnesium in dehydrogenation catalysts. U.S. Pat. No. 3,205,179 to Soderquist et al., issued Sept. 7, 1965, disclosed the use of cadmium, aluminum, magnesium and other metals in dehydrogenation catalysts. U.S. Pat. Nos. 2,971,927 to Price, issued Feb. 14, 1961; 2,971,926 to Stillwell, issued Feb. 14, 1961; 2,603,610 to Amos et al., issued July 15, 1952; 2,414,585 to Eggertsen et al., issued Jan. 21, 1947; 2,460,811 to Davies et al., issued Feb. 8, 1949 and 2,461,147 to Davies et al., issued Feb. 8, 1949 are references that disclosed a number of metals used in dehydrogenation catalysts.

The prior art has disclosed a large number of metals that are used as catalysts, stabilizers, activators and promoters for dehydrogenation reactions. None of the prior art references, however, disclose, suggest or teach that when certain oxidic metal compounds are combined with iron-potassium-vanadium oxides and optionally chromium oxide, a catalyst which improves the process for the dehydrogenation of hydrocarbons is provided.

STATEMENT OF INVENTION

It has now been found that in the process for effecting a continuous dehydrogenation of hydrocarbons to more unsaturated hydrocarbons at about 500° C. to about 700° C. improved selectivities and/or conversions are obtained by carrying out the process in the presence of a catalyst comprising iron oxide, potassium oxide, carbonate or mixtures thereof, vanadium oxide, optionally chromium oxide and an oxide selected from the group consisting of an oxide of aluminum, cadmium, magnesium, manganese, nickel, a member of the rare earth series and mixtures thereof. The process of this invention is of particular use in producing alkenyl aromatic hydrocarbons from alkyl aromatic hydrocarbons particularly lower alkenyl aromatic hydrocarbons from lower alkyl aromatic hydrocarbons as for example, ethyl benzene, isopropylbenzene, diethylbenzene and ethyl methyl benzene, where the lower alkenyl and lower alkyl groups have from two to six carbon atoms, and specifically is useful for the production of styrene from ethyl benzene.

DETAILED DESCRIPTION OF THE INVENTION

The catalysts utilized in the process of this invention typically contain (a) from about 50 to about 95 and preferably from about 55 to about 90 percent by weight of iron compound, measured as ferric oxide, (b) from about 5 to about 30 and preferably from about 6 to about 25 percent by weight of potassium compound, measured as potassium oxide, (c) optionally up to about 30 (i.e., from 0 to about 30) and preferably up to about 20 (i.e., from about 0 to about 20) percent by weight of chromium compound measured as chromic oxide ($Cr_2O_3$), (d) from about 0.01 to about 9 preferably from about 0.1 to about 9 and most preferably from about 0.2 to about 6 percent by weight of vanadium compound measured as vanadium pentoxide and (e), from about 0.01 to about 10, preferably from about 0.1 to about 10, more preferably from about 0.1 to about 5, even more preferably from about 0.3 to about 4, and most preferably from about 0.5 to about 3 percent by weight of an additive compound selected from the group consisting of compounds of aluminum, cadmium, magnesium, manganese, nickel, uranium, a member of the rare earth series, and mixtures thereof measured as the individual oxide which is the most stable form in air at one atmosphere pressure and 25° C. Alternately stated, these catalysts contain (a) from about 35 to about 67 and preferably from about 38 to about 63 percent by weight of an iron oxide compound, measured as iron metal oxide, (b) from about 4 to about 25 and preferably from about 5 to about 21 percent by weight of potassium oxide, measured as potassium metal, (c) optionally up to about 21 (i.e., from 0 to about 21) and preferably up to about 14 (i.e., from about 0 to about 14) percent by weight of a chromium oxide measured as chromium metal (d) from about 0.005 to about 5 preferably from about 0.05 to about 5 and most preferably from about 0.1 to about 4 percent by weight of a vanadium oxide measured as vanadium metal and (e), from about 0.005 to about 9, preferably from about 0.05 to about 9, more preferably from about 0.05 to about 5, even more preferably from about 0.1 to about 4, and most preferably from about 0.2 to about 3 percent by weight of an additive oxide selected from the group consisting of an oxide of aluminum, cadmium, magnesium, manganese, nickel, uranium, a member of the rare earth series, and mixtures thereof, measured as the individual metal.

Variances within the general composition described above depend in part on whether the catalyst is used to produce vinyl aromatic compounds or olefinic compounds.

Catalysts for the production of vinyl aromatic compounds such as styrene from ethyl benzene and alphamethylstyrene from cumene typically contain from about 75 to about 95 and preferably from about 80 to about 90 percent by weight of iron compound measured as ferric oxide, from about 6 to about 25, preferably from about 5 to about 20 and more preferably from about 6 to about 15 percent by weight of potassium compound measured as potassium oxide, optionally up to about 30, preferably up to about 20 and more preferably up to about 10 percent by weight of chromium compound measured as chromic oxide, ($Cr_2O_3$), from about 0.01 to about 9, preferably from about 0.2 to about 6 percent by weight of vanadium compound measured as vanadium pentoxide and from about 0.01 to about 10, preferably from about 0.1 to about 10, more preferably from about 0.1 to about 5, even more preferably from about 0.3 to about 4 and most preferably from about 0.5 to about 3 percent by weight of an additive compound selective from the group consisting of compounds of aluminum, cadmium, magnesium, manganese, nickel, uranium, a member of the rare earth series and mixtures thereof measured as the individual oxide which is the most stable in air at one atmosphere pressure and 25° C. Alternately stated, these catalysts contain from about 52 to about 67 and preferably from about 56 to about 63 percent by weight of an iron oxide measured as iron metal, from about 5 to about 21, preferably from about 4 to about 17 and more preferably from about 5 to about 13 percent by weight of potassium oxide measured as potassium metal, optionally up to about 21, preferably up to about 14 and more preferably up to about 7 percent by weight of a chromium oxide measured as chromium metal, from about 0.005 to about 5, preferably from about 0.05 to 5 and more preferably from about 0.1 to about 4 percent by weight of a vanadium oxide measured as vanadium metal and from about 0.005 to about 9, preferably from about 0.05 to about 9, more preferably from about 0.05 to about 5, even more preferably from about 0.1 to about 4 and most preferably from about 0.2 to about 3 percent by weight of an additive oxide selected from the group consisting of an oxide of aluminum, cadmium, magnesium, manganese, nickel, uranium, a member of the rare earth series and mixtures thereof, measured as the individual metal.

Catalysts for the production of dienes from mono-olefins such as, for example, isoprene from amylene or butadiene from butylene typically contain from about 50 to about 75 and preferably from about 55 to about 70 percent by weight of iron compound measured as ferric oxide, from about 15 to about 30 and preferably from about 20 to about 30 percent by weight of potassium compound measured as potassium oxide, optionally up to about 30, preferably up to about 20 and more preferably up to about 10 percent by weight of chromium compound measured as chromic oxide ($Cr_2O_3$), from about 0.01 to about 9, preferably from about 0.1 to about 9 and more preferably from about 0.2 to about 6 percent by weight of vanadium compound measured as vanadium pentoxide and from about 0.01 to about 10, preferably from about 0.1 to about 10, more preferably from about 0.1 to about 5, even more preferably from about 0.3 to about 5, yet even more preferably from about 0.3 to about 4 and most preferably from about 0.5 to about 3 percent by weight of an additive compound selected from the group consisting of compounds of aluminum, cadmium, magnesium, manganese, nickel, uranium, a member of the rare earth series and mixtures thereof measured as the individual oxide which is the most stable in air at one atmosphere pressure and 25° C. Alternately stated, these catalysts contain from about 35 to about 53 and preferably from about 38 to about 49 percent by weight of an iron oxide measured as iron metal, from about 12 to about 25 and preferably from about 16 to about 25 percent by weight of potassium oxide measured as potassium metal, optionally up to about 21, preferably up to about 14 and more preferably up to about 7 percent by weight of a chromium oxide measured as chromium metal, from about 0.005 to about 5, preferably from about 0.05 to about 5 and more preferably from about 0.1 to about 4 percent by weight of a vanadium oxide measured as vanadium metal and from about 0.005 to about 9, preferably from about 0.05 to about 9, more preferably from about 0.05 to about 5, even more preferably from about 0.1 to about 5, yet even more preferably from about 0.1 to about 4 and most preferably from about 0.2 to about 3 percent by weight of an additive oxide selected from the group consisting of an oxide of aluminum, cadmium, magnesium, manganese, nickel, uranium, a member of the rare earth series and mixtures thereof, measured as the individual metal.

It is known that the most selective catalysts are those having surface areas below 10 sq. meter per gram, and in many cases below 5 sq. meter/gram. If iron oxides have surface areas in excess of this requirement, the surface area can be reduced by precalcining the iron oxides at temperatures exceeding 700° C. for a period of time ranging from one-half hour to several hours.

The strength of the catalysts can be improved by adding binding agents such as calcium aluminate and portland cement. However, catalyst strength can also be improved by calcining the extruded pellets at temperatures ranging from about 700° C. to about 1000° C. Calcination at these temperatures can alleviate the use of binding agents.

While most of the above methods result in catalysts having desired surface area, they also result in catalysts having a relatively high density. It has been found that catalysts having a highly porous structure and a low surface area are highly active in catalytic dehydrogenation. Various methods have been employed to form highly porous catalysts. For example, combustible materials, such as sawdust, carbon, wood flour, etc., have been added during catalyst formation, and then burned out after the pellet has been formed. Many of these porosity-promoting aids also assist in facilitating extrusion of pellets, for example, the use of graphite and aqueous solutions of methyl cellulose.

Many forms of iron oxide can be used in preparation of the catalyst used in the process of this invention. Typically, iron oxides employed in catalyst preparations of this sort are usually a synthetically produced, powdered red, red-brown, yellow or black pigment. The red or red-brown pigments are highly pure ferric oxide, while the black pigment is the magnetic form, ferrosoferric oxide ($Fe_3O_4$), which is usually found in the catalyst under various reaction conditions. The yellow iron oxides consist of the monohydrated form of ferric oxide. These oxides are prepared by various methods, e.g., oxidation of iron compounds, roasting, precipitation, calcination, etc. A suitable form of iron compound is the mono-hydrated yellow iron oxide used in the preparation of catalysts according to U.S. Pat. Nos. 3,360,597, issued Dec. 26, 1967, and 3,364,277, issued Jan. 16, 1968. Particularly suitable are pigment grade red iron oxides of purities exceeding 98% wt. These red oxides have surface areas ranging from 2 to 50 $m^2$/gram and particle sizes from 0.1 to 2 microns. The iron compound is present in the catalyst in either one or a mixture of both of its possible oxidation, states, i.e., as ferrous iron or ferric iron or mixtures thereof, as for example, ferrosoferric iron. The iron compound present is conveniently measured as ferric oxide.

The potassium promoter is added to the catalyst in various forms. For example, it may be added as the oxide, or as other compounds which are convertible, at least in part, under calcination conditions, to the oxides, such as the hydroxides, the carbonates, the bicarbonates, the phosphates, the borates, the acetates, and the like. A particularly preferred potassium compound is potassium carbonate. The potassium compound is present in the catalyst as a potassium oxide, a potassium carbonate or a mixture thereof. High carbon dioxide partial pressures in the reaction gases will favor high carbonate to oxide ratios and vice versa. The potassium compound(s) is conveniently measured as potassium oxide.

Chromium oxide has been typically added to alkali-promoted iron oxide catalysts to extend their life. Environmental and toxicity considerations may militate against the use of chromium compounds in favor of somewhat shorter catalyst life under certain conditions. However, chromium, when optionally used in the catalyst of this invention is added to the catalyst in the form of a chromium oxide or in the form of chromium compounds which decompose upon calcination to the oxides, as for example chromium nitrates, hydroxides, acetates, and the like. Preferred amounts of chromium oxide added range from about 0.01 to about 10 and more preferably from about 0.1 to about 10.

Vanadium is added to the catalyst as vanadium pentoxide or as salts or other compounds thermally decomposable to the oxides, such as sulfates, oxysulfates, sulfides, or vanadates. The vanadium is present in the catalyst in one or mixtures of more than one of its possible oxidation states, the pentavalent state being the preferred state. The vanadium compound(s) is conveniently measured as the vanadium pentoxide.

The aluminum compound is added to the catalyst in the form of aluminum oxide or in the form of aluminum compounds which decompose upon calcination to the oxides, as for example aluminum hydroxides, hydrated oxides, nitrates, acetates, alcoholates and the like.

The cadmium, magnesium, manganese, nickel, and uranium, compounds are added to the catalyst in the form of their respective oxides or in the form of compounds which decompose upon calcination to the oxides, as for example, the hydroxides, carbonates, bicarbonates, nitrates, acetates and the like.

The rare earth series of metal compounds used in this invention includes those metals having atomic numbers ranging from and including number 58 up to and including number 71, i.e., from cerium to lutetium. Preferred species are cerium, praseodymium and neodymium. The rare earth compounds are added to the catalyst in the form of their oxides or in the form of compounds which decompose upon calcination to the oxides, as for example the hydroxides, carbonates, bicarbonates, nitrates acetates and the like.

The catalyst used in the process of this invention will consist of mixtures of oxides, both simple oxides such as ferric oxide and complex oxides such as the spinels and ferrites as well as oxides such as vanadates, etc., and carbonates, with carbonates of potassium preferred. Specific oxides present in the calcined catalyst will be determined by calcining conditions, reaction conditions, etc. Typical calcining conditions range from about 500° C. to about 1100° C. Since typical commercial dehydrogenation reactions are carried out in the presence of steam and carbon dioxide, the catalyst contains a proportion of carbonates and some hydroxides. The catalyst of this invention comprises a mixture of oxides and carbonates having from about 50 to about 95 percent by weight of an iron oxide, measured as ferric oxide; from about 5 to about 30 percent by weight of a potassium compound selected from the group consisting of a potassium oxide, a potassium carbonate, or mixtures thereof, measured as potassium oxide; from about 0.01 to about 9 percent by weight of a vanadium oxide, measured as vanadium pentoxide, optionally up to 30 percent by weight of a chromium oxide measured as chromic oxide and from about 0.01 to about 10 percent by weight of an additive oxide selected from the group consisting of oxides of aluminum, cadmium, magnesium, nickel, uranium, a member of the rare earth series and mixtures thereof measured as the individual oxide having the most stable form in air at one atmosphere pressure and 25° C.

The catalysts used in the process of this invention are autoregenerative under conditions at which the dehydrogenation reaction is effected, that is, they are capable of being continually regenerated under the conditions of the reaction.

The catalysts used in the process of this invention are compounded in a variety of ways. One method is to ballmill together a mixture of the desired oxides and/or compounds decomposable upon calcination to oxides, adding a small amount of water, and extruding the paste formed to produce small pellets, which are then dried and calcined at temperatures above 500° C. Another method is to dissolve the components together, spray dry these components to form a resulting powder, calcine the powder into the resultant oxides, and then add sufficient water to form a paste and extrude into pellets, dry and calcine. Another procedure would involve precipitating those materials which are precipitatable, such as iron and chromium, as the resultant hydroxides, partially de-watering the resultant precipitate, adding soluble salts of the other required metals, and then subsequently extruding, drying and calcining the resultant pellets. A preferred method is to dry-blend powders of oxides and/or compounds decomposable upon calcination to the oxides, add water, optionally containing dissolved therein soluble compounds decomposable upon calcination to the oxides, then mixing and/or mulling the resultant paste, pelletizing the mixture, subsequently substantially drying at a temperature from about 50° C. to about 300° C. and then calcining the pellets at a temperature ranging from about 500° C. to about 1100° C., preferably from about 600° C. to about 1000° C. to form the final product. The drying and calcining could be carried out stepwise in the same furnace by suitable programming of the temperature. Alternatively, water-insoluble dry powders of oxides and/or compounds decomposable upon calcination to the oxides are dry-mixed, and the balance of the other materials needed are dissolved in water and the resultant solution is used to form the paste with the dry powders. There are many variations of the mixing of dry powders, water and water soluble compounds that give equivalent results and fall within the scope of this invention.

The optimum size of the pellets produced will vary according to the need of various process. Catalysts pellets having a diameter of from ⅛ to ⅜ of an inch, and from ⅛ to ⅜ of an inch in length are typical. The smaller diameter catalysts are generally more active but provide increased pressure drops.

The dehydrogenation reaction is usually carried out at reaction temperatures of about 500°–700° C. However, higher or lower temperatures may be used without departing from the scope of this invention. The use of atmospheric, sub-atmospheric, or super-atmospheric pressure is suitable. However, it is preferable to operate at as low a pressure as is feasible, and atmospheric or subatmospheric pressure is preferred. The process of the invention may be carried out in batch, semi-continuous, or continuous operation, with continuous operation being preferred. The catalyst is employed in the form of a fixed bed, or in fluidized or suspended form. It is preferable to utilize a fixed bed. The reaction may be carried out in single stage reactors or by staging in series reactors. The reactors may be of various designs, e.g., downflow reactors, radial reactors, etc.

With the use of the catalyst of this invention, it is desirable to add steam to the reactant feed to aid in the removal of carbonaceous residues from the catalyst. The reaction feed contains from 2–30 moles of steam for every mole of feed. Catalysts having higher potassium contents are usually employed at lower feed to steam ratios. Feed to steam ratios of from about 1:9 to about 1:18 are desirable. Good results are obtained with feed to steam ratios of about 1:12 to about 1:18.

The contact time of the reactant gas with the catalyst is usually defined in terms of gaseous-hourly-space velocity (volumes of hydrocarbon reactant per volume of catalyst per hour, i.e., GHSV). The GHSV according to this invention may vary from about 10 to 3,000 and is preferably adjusted within this range to effect the degree of conversion desired for the particular feed in question.

The preparation of catalysts and their use in the process of this invention will be further described by the following illustrative embodiments which are provided for illustration and are not to be construed as limiting the invention. It should be noted that advantages resulting from increases of selectivity of only one or two percentage points are extremely significant in a commercial process which may produce many hundreds of thousand pounds of product a day. Catalysts with higher activities, which can result in lower operating temperatures can be significant in lowering costs of plant operations.

ILLUSTRATIVE EMBODIMENT I

A catalyst for use in the process of this invention was prepared by dry-blending magnesium carbonate, vanadium pentoxide, chromium oxide, potassium carbonate with red iron oxide having a surface area of about 5 $m^2/gm$ and an average particle size of 1 micron. Water was then added and the mixture was mulled and pelleted. The pellets were dried at 200° C. for 1/3 of an hour and then calcined at a temperature ranging from 800°–960° C. for about 50 minutes. This catalyst is denoted at 1 in Table I which gives the resultant composition.

Catalysts numbers 2–38 were prepared similar to the catalyst above except that the appropriate starting additive, listed in the last column of Table 1, was substituted for the magnesium carbonate. Catalysts 10 and 13 were prepared in a similar fashion except that the chromium oxide was omitted.

Catalyst number 27 contains only iron-potassium-chromium vanadium oxides.

Catalysts 28 and 29 contains only iron-potassium-chromium oxides and catalyst 29 is known commercially as Shell 105 ® Catalyst.

TABLE I

CATALYST COMPOSITIONS

Composition, W % (Balance $Fe_2O_3$)

| Cat. No. | % $K_2O$ | % $Cr_2O_3$ | % $V_2O_5$ | % Additive | Additive Form |
|---|---|---|---|---|---|
| 1 | 12.5 | 2.5 | 3.0 | 0.90 MgO | $MgCO_3$ |
| 2 | 12.5 | 2.5 | 3.0 | 1.3 MgO | $MgCO_3$ |
| 3 | 12.5 | 2.5 | 3.0 | 2.6 MgO | $MgCO_3$ |
| 4 | 12.5 | 2.5 | 3.0 | 3.9 MgO | $MgCO_3$ |

TABLE I-continued

CATALYST COMPOSITIONS

Composition, W % (Balance $Fe_2O_3$)

| Cat. No. | % $K_2O$ | % $Cr_2O_3$ | % $V_2O_5$ | % Additive | Additive Form |
|---|---|---|---|---|---|
| 5 | 12.5 | 2.5 | 3.0 | 6.9 $Ce_2O_3$ | $Ce(NO_3)_3 \cdot 6H_2O$ |
| 6 | 12.5 | 2.5 | 3.0 | 5.4 $Ce_2O_3$ | $Ce(NO_3)_3 \cdot 6H_2O$ |
| 7 | 12.5 | 2.5 | 3.0 | 1.7 ZnO | $ZnCO_3$ |
| 8 | 12.5 | 2.5 | 3.0 | 3.4 ZnO | $ZnCO_3$ |
| 9 | 12.6 | 2.5 | 3.0 | 3.4 ZnO | $ZnCO_3$ |
| 10 | 12.6 | 0 | 3.0 | 3.4 ZnO | $ZnCO_3$ |
| 11 | 12.5 | 2.5 | 3.0 | 1.7 CuO | $CuCO_3$ |
| 12 | 12.6 | 2.5 | 3.9 | 1.7 CuO | $CuCO_3$ |
| 13 | 12.6 | 0 | 3.9 | 1.7 CuO | $CuCO_3$ |
| 14 | 12.5 | 2.5 | 3.0 | 2.7 CdO | $CdCO_3$ |
| 15 | 12.5 | 2.5 | 3.0 | 5.7 $UO_3$ | $UO_2(C_2H_3O_2) \cdot 2H_2O$ |
| 16 | 12.5 | 2.5 | 3.0 | 3.0 $UO_3$ | $UO_2(C_2H_3O_2) \cdot 2H_2O$ |
| 17 | 12.6 | 2.5 | 3.6 | 0.8 MnO | $MnCO_3$ |
| 18 | 12.5 | 2.5 | 3.0 | 1.5 MnO | $MnCO_3$ |
| 19 | 12.5 | 2.5 | 3.0 | 3.0 MnO | $MnCO_3$ |
| 20 | 12.6 | 2.5 | 3.0 | 4.3 $Al_2O_3$ | $Al_2O_3 \cdot 3H_2O$ |
| 21 | 12.6 | 2.5 | 3.0 | 4.3 $Al_2O_3$ | 50% Al stearate + 50% $Al_2O_3 \cdot H_2O$ |
| 22 | 12.6 | 2.5 | 3.0 | 7.1 $Pr_2O_3$ | $Pr_2O_3$ |
| 23 | 12.6 | 2.5 | 3.0 | 7.2 $Nd_2O_3$ | $Nd_2O_3$ |
| 24 | 12.5 | 2.5 | 3.0 | 3.5 NiO | $NiCO_3$ |
| 25 | 12.5 | 2.5 | 3.0 | 0.8 NiO | $NiCO_3$ |
| 26 | 12.5 | 2.5 | 3.0 | 0.4 NiO | $NiCO_3$ |
| 27 | 12.5 | 2.5 | 3.0 | 0 | 0 |
| 28 | 12.6 | 2.5 | 0 | 0 | 0 |
| 29 | 9.6 | 2.5 | 0 | 0 | 0 |
| 30 | 12.5 | 2.5 | 3.0 | 2.4 CaO | $CaCO_3$ |
| 31 | 12.5 | 2.5 | 3.0 | 7.4 PbO | $PbCO_3$ |
| 32 | 12.5 | 2.5 | 3.0 | 1.7 $SnO_2$ | $SnO_2$ |
| 33 | 12.5 | 2.5 | 3.0 | 4.9 $WO_3$ | $(NH_4)_6H_2W_{12}O_{40} \cdot H_2O$ |
| 34 | 12.5 | 2.5 | 3.0 | 5.6 $ThO_2$ | $ThCO_3$ |
| 35 | 12.5 | 2.5 | 3.0 | 9.6 $Tl_2O_3$ | Tl Formate |
| 36 | 12.5 | 2.5 | 3.0 | 2.6 $ZrO_2$ | Zr Acetate |
| 37 | 12.5 | 2.5 | 3.0 | 5.3 $Sb_2O_3$ | $K_2SbO_3$ |
| 38 | 12.3 | 2.5 | 3.0 | 5.1 BaO | $BaCO_3$ |

The catalysts listed in Table I were tested for activity and selectivity in the dehydrogenation of ethylbenzene to styrene by placing the catalyst pellets in a fixed reactor having a volume of 100 cc and passing a preheated mixture of steam and ethylbenzene at a molar ratio of 12:1 into the catalyst bed which was maintained at the temperature needed to effect the desired conversion of ethylbenzene. This temperature is dependent upon the activity of the catalyst. A pressure of about 0 to 1.5 inches of water was used and the liquid hourly space velocity of ethylbenzene was varied from about 0.65 to about $1.8h^{-1}$. The condensed liquid products were analyzed for styrene, ethylbenzene, benzene and toluene. These results were converted to activity and selectivity and are recorded in Table II. In Table II and hereinafter $T_{(70)}$ is used to represent the temperature in ° C. at 70 percent ethylbenzene conversion, and $S_{(70)}$ is used to represent the percent molar selectivity to styrene at 70 molar percent ethylbenzene conversion. $T_{(70)}$ is the indicium of activity, the higher the temperature, the lower the activity.

TABLE II

DEHYDROGENATION RESULTS

| Cat. No. | $T_{(70)}$ | $S_{(70)}$ |
|---|---|---|
| 1 | 607 | 91.8 |
| 2 | 608 | 91.5 |
| 3 | 602 | 92.5 |
| 4 | 608 | 91.5 |
| 5 | 610 | 92.2 |
| 6 | 604 | 92.5 |
| 7 | 608 | 91.4 |
| 8 | 607 | 92.5 |
| 9* | 606 | 92.1 |
| 10* | 600 | 92.7 |
| 11 | 620 | 92.4 |
| 12* | 618 | 91.2 |
| 13* | 616 | 91.8 |
| 14 | 610 | 91.4 |
| 15 | 606 | 91.0 |
| 16 | 600 | 90.0 |
| 17 | 602 | 91.0 |
| 18 | 606 | 91.4 |
| 19 | 618 | 91.0 |
| 20 | 609 | 91.1 |
| 21 | 605 | 92.0 |
| 22 | 616 | 91.3 |
| 23 | 611 | 92.1 |
| 24 | 614 | 91.0 |
| 25 | 603 | 92.2 |
| 26 | 606 | 92.5 |
| 27 | 630 | 91.1 |
| 28 | 598 | 88.2 |
| 29 | 595 | 87.7 |
| 30 | 642 | 91.4 |
| 31 | >650 | (inactive) |
| 32 | 622 | 90.8 |
| 33 | >650 | (inactive) |
| 34 | 624 | 93.1 |
| 35 | 624 | 93.0 |
| 36 | 613 | 89.9 |
| 37 | >640 | 83.0 |
| 38 | 618 | 89.5 |

*All catalysts calcined for about 50 minutes at 800–940° C except catalysts marked with a * which were calcined for 1 hour at 815° C.

What is claimed is:

1. In a process for effecting a continuous dehydrogenation of hydrocarbons to more unsaturated hydrocarbons at a temperature between about 500° C. and about 700° C., the improvement which comprises effecting the dehydrogenation with a catalyst comprising a mixture having:

(a) from about 50 to about 95 percent by weight of an iron oxide, measured as ferric oxide;

(b) from about 5 to about 30 percent by weight of a potassium compound selected from the group consisting essentially of potassium oxide, potassium carbonate, and mixtures thereof, measured as potassium oxide;

(c) from about 0.01 to about 9 percent by weight of a vanadium oxide, measured as vanadium pentoxide, (d) from about 0.01 to about 10 percent by weight of an additive oxide selected from the group consisting of an oxide of cadmium, magnesium, manganese, nickel, a member of a rare earth series, uranium, and mixtures thereof measured as the individual oxide having the most stable form in air at one atmosphere and 25° C., and (e) from 0 to about 30 percent by weight of a chromium oxide measured as chromic oxide.

2. The process of claim 1 wherein the additive oxide is selected from the group consisting of cadmium, magnesium, manganese, nickel, uranium and mixtures thereof.

3. The process of claim 2 wherein the additive oxide is selected from the group consisting of cadmium, manganese, nickel, and mixtures thereof.

4. The process of claim 2 wherein the additive oxide is selected from the group consisting of magnesium, uranium and mixtures thereof.

5. The process of claim 1 wherein the additive oxide is selected from the group consisting of the rare earth series and mixtures thereof.

6. The process of claim 1 wherein the chromium oxide ranges from 0 to about 20 percent by weight.

7. The process of claim 6 wherein the additive oxide is selected from the group consisting of cadmium, magnesium, manganese, nickel, uranium, and mixtures thereof.

8. The process of claim 7 wherein the additive oxide is selected from the group consisting of cadmium, manganese, nickel, and mixtures thereof.

9. The process of claim 7 wherein the additive oxide is selected from the group consisting of magnesium, uranium and mixtures thereof.

10. The process of claim 6 wherein the additive oxide is selected from the group consisting of the rare earth series and mixtures thereof.

11. The process of claim 1 wherein the hydrocarbon is an alkyl aromatic hydrocarbon, and the more unsaturated hydrocarbon is an alkenyl aromatic hydrocarbon, the iron oxide ranges from about 75 to about 95 percent by weight, and the potassium compound ranges from about 6 to about 25 percent by weight.

12. The process of claim 11 wherein the alkyl aromatic hydrocarbon is ethylbenzene and the alkenyl aromatic hydrocarbon is styrene.

13. The process of claim 12 wherein the additive oxide is selected from the group consisting of cadmium, magnesium, manganese, nickel, uranium, and mixtures thereof.

14. The process of claim 13 wherein the additive oxide is selected from the group consisting of cadmium, manganese, nickel, and mixtures thereof.

15. The process of claim 13 wherein the additive oxide is selected from the group consisting of magnesium, uranium and mixtures thereof.

16. The process of claim 12 wherein the additive oxide is selected from the group consisting of the rare earth series and mixtures thereof.

17. The catalyst of claim 12 wherein the chromium oxide ranges from 0 to about 20 percent by weight.

18. The process of claim 1 wherein the catalyst is prepared by combining iron, potassium, optionally chromium, vanadium and additive oxides and/or compounds thermally decomposable to oxides upon calcination with water to form a paste, forming the paste into pellets, drying the pellets and then calcining the pellets at a temperature from about 600° C. to about 1000° C.

19. The process of claim 18 wherein the drying and calcining are performed sequentially in one step.

20. The process of claim 12 wherein the catalyst is prepared by combining iron, potassium, optionally chromium, vanadium and additive oxides and/or compounds thermally decomposable to oxides upon calcination with water to form a paste, forming the paste into pellets, drying the pellets and then calcining the pellets at a temperature ranging from about 600° C. to about 1000° C.

21. The process of claim 20 wherein the drying and calcining are performed sequentially in one step.

* * * * *